US008968180B2

(12) United States Patent
Woodruff et al.

(10) Patent No.: US 8,968,180 B2
(45) Date of Patent: Mar. 3, 2015

(54) APPARATUS FOR COMPLETING IMPLANTATION OF GASTRIC BAND

(75) Inventors: Scott A. Woodruff, Cincinnati, OH (US); John B. Schulte, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 918 days.

(21) Appl. No.: 12/637,138

(22) Filed: Dec. 14, 2009

(65) Prior Publication Data

US 2011/0144420 A1 Jun. 16, 2011

(51) Int. Cl.
*A61F 5/00* (2006.01)
*A61F 5/01* (2006.01)

(52) U.S. Cl.
CPC .......... *A61F 5/0066* (2013.01); *A61F 5/0056* (2013.01); *A61F 5/0089* (2013.01)
USPC .......................................................... 600/37

(58) Field of Classification Search
USPC .................................... 600/37; 606/140, 206
See application file for complete search history.

(56) References Cited

U.S. PATENT DOCUMENTS

| 5,522,788 | A | 6/1996 | Kuzmak |
| 6,067,991 | A | 5/2000 | Forsell |
| 6,461,292 | B1 | 10/2002 | Forsell |
| 6,470,892 | B1 | 10/2002 | Forsell |
| 7,351,240 | B2 | 4/2008 | Hassler, Jr. et al. |
| 7,390,294 | B2 | 6/2008 | Hassler, Jr. |
| 7,416,528 | B2 | 8/2008 | Crawford et al. |
| 7,442,165 | B2 | 10/2008 | Forsell |
| 7,621,863 | B2 | 11/2009 | Forsell |
| 7,771,439 | B2 * | 8/2010 | Griffiths ........................ 606/139 |
| 8,070,673 | B2 * | 12/2011 | Gertner et al. ................... 600/37 |
| 8,182,411 | B2 * | 5/2012 | Dlugos ............................ 600/37 |
| 8,236,009 | B2 * | 8/2012 | Saadat et al. ................... 606/139 |
| 2005/0283118 | A1 | 12/2005 | Uth et al. |
| 2006/0178564 | A1 * | 8/2006 | Jones et al. ..................... 600/159 |
| 2006/0271074 | A1 * | 11/2006 | Ewers et al. ................... 606/148 |
| 2007/0185505 | A1 * | 8/2007 | Hart ............................... 606/148 |
| 2007/0185518 | A1 | 8/2007 | Hassler, Jr. |
| 2007/0186933 | A1 * | 8/2007 | Domingo et al. ......... 128/207.15 |
| 2007/0288048 | A1 | 12/2007 | Ortiz et al. |
| 2008/0146869 | A1 * | 6/2008 | Chow et al. ...................... 600/37 |
| 2009/0088792 | A1 * | 4/2009 | Hoell et al. .................... 606/206 |
| 2009/0157076 | A1 * | 6/2009 | Athas et al. ..................... 606/41 |

FOREIGN PATENT DOCUMENTS

| EP | 1 520 563 | 4/2005 |
| EP | 1 864 625 | 12/2007 |

OTHER PUBLICATIONS

International Search Report dated Mar. 10, 2011 for Application No. PCT/US2010/059129.

* cited by examiner

*Primary Examiner* — Charles A Marmor, II
*Assistant Examiner* — Thaddeus Cox
(74) *Attorney, Agent, or Firm* — Frost Brown Todd LLC

(57) ABSTRACT

An instrument comprises a handle, an articulating shaft, an end effector, and a translatable hook member. The shaft defines a side aperture, proximal to an articulating section of the shaft, through which the hook member protrudes when the hook member is translated distally. The end effector is used to form a retrogastric tunnel through blunt dissection in tissue near a patient's gastro-esophageal junction; and then to pull a gastric band through the tunnel to position the gastric band about the gastro-esophageal junction. The end effector is then used to hold a first portion of the gastric band in place while the hook member is extended distally to engage a second portion of the gastric band. The hook member may then be retracted proximally to couple the second portion of the gastric band with the first portion of the gastric band, thereby latching the gastric band in place.

18 Claims, 8 Drawing Sheets

APPARATUS FOR COMPLETING IMPLANTATION OF GASTRIC BAND

BACKGROUND

A variety of systems and devices have been made and used for treating morbid obesity. Some such systems and devices include adjustable gastric band systems, which are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of gastric bands are disclosed in U.S. Pat. No. 7,416,528, entitled "Latching Device for Gastric Band," issued Aug. 26, 2008, the disclosure of which is incorporated by reference herein. Another example of such an adjustable gastric band is disclosed in U.S. Pat. No. 6,067,991, entitled "Mechanical Food Intake Restriction Device," issued May 30, 2000, the disclosure of which is incorporated by reference herein.

In addition, a variety of devices and methods have been made and used for installing a gastric band. For instance, examples of such devices and methods are disclosed in U.S. Pub. No. 2007/0185518, entitled "Method for Aiding a Surgical Procedure," published Aug. 9, 2007, the disclosure of which is incorporated by reference herein. Additional examples of such devices and methods are disclosed in U.S. Pub. No. 2007/0288048, entitled "Articulating Blunt Dissector/Gastric Band Application Device," published Dec. 13, 2007, now U.S. Pat. No. 7,763,039, issued Jul. 27, 2010, the disclosure of which is incorporated by reference herein. In some settings, conventional surgical graspers are used to install a gastric band, in addition to or in lieu of the devices described in the above-referenced publications. Installation of a gastric band may include first positioning the gastric band in place and then securing the gastric band in place.

While a variety of devices and methods have been made and used to install a gastric band, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
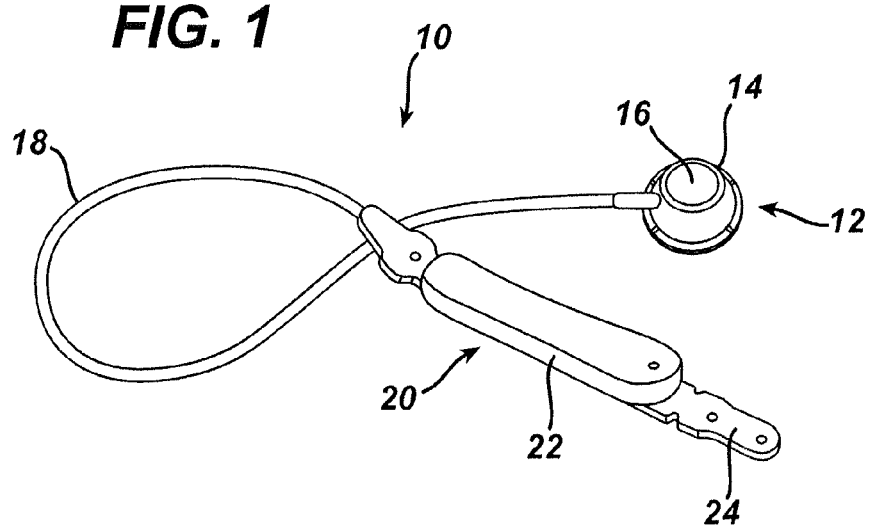
FIG. 1 depicts a perspective view of an implantable portion of an exemplary gastric band system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Overview

FIGS. 1-4 illustrate an exemplary gastric band system (10). As shown, gastric band system (10) comprises an injection port (12), a gastric band (20), and a catheter (18). Injection port (12) of the present example comprises a housing (14) and a needle penetrable septum (16). Housing (14) defines a fluid reservoir (not shown), such that a needle may pierce septum (16) to reach the reservoir and add or withdraw fluid (e.g., saline, etc.) as described in greater detail below. Housing (14) may be formed of titanium, plastic, or any other suitable material or combination of materials. Septum (16) may be formed of silicone or any other suitable material or combination of materials. Injection port (12) may be subcutaneously secured over a patient's sternum, to the patient's abdominal fascia, or in any other suitable location. In some versions, injection port (12) is configured and operable in accordance with the teachings of U.S. Pub. No. 2005/0283118, entitled "Implantable Medical Device with Simultaneous Attachment Mechanism and Method," published Dec. 22, 2005, the disclosure of which is incorporated by reference herein. Alternatively, injection port (12) may have any other suitable configuration and/or operability.

Gastric band (20) of the present example comprises an inflatable bladder (22) that is secured to a flexible strap (24) Inflatable bladder (22) may be formed of silicone or any other suitable material or combination of materials. Catheter (18) provides fluid communication between bladder (22) and the reservoir of injection port (12). Accordingly, a needle that is inserted through septum (16) may be used to add or withdraw fluid from inflatable bladder (22), to adjust the restriction created by gastric band (20) as described in greater detail below. In some versions, gastric band (20) is configured and operable in accordance with the teachings of U.S. Pat. No. 7,416,528, entitled "Latching Device for Gastric Band," issued Aug. 26, 2008, the disclosure of which is incorporated by reference herein. Alternatively, gastric band (20) may have any other suitable configuration and/or operability.

Figure 2:
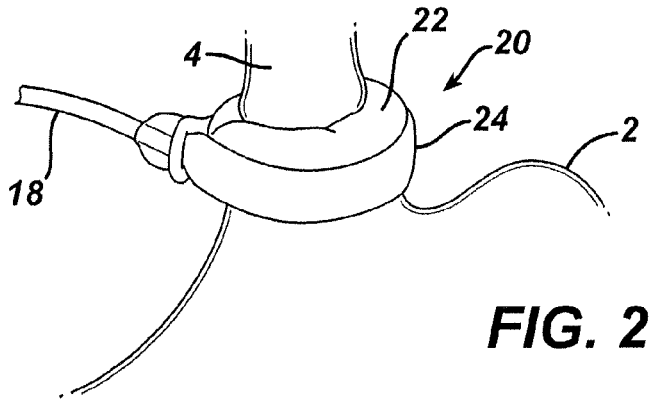
FIG. 2 depicts a perspective view of the gastric band of FIG. 1, showing the band positioned around the gastro-esophageal junction of a patient.

In some settings, gastric band (20) is applied about the gastro-esophageal junction of a patient. In particular, and as shown in FIG. 2, gastric band (20) is installed such that bladder (22) is adjacent to the tissue of the gastro-esophageal junction, with strap (24) on the outside of bladder (22). The ends of strap (24) are secured relative to each other when gastric band (20) is sufficiently wrapped about the patient's stomach (2). While strap (24) is flexible in this example, strap (24) substantially resists stretching along its length. Accordingly, when fluid is added to bladder (22) (e.g., using a needle inserted through septum (16) of injection port (12), etc.), bladder (22) expands and exerts inward forces on the gastroesophagel junction of the patient. This reduces the size of the internal stoma at the gastro-esophageal junction, thereby creating a restriction on food intake into the patient's stomach (2). It should be understood that the size of this stoma may be decreased by adding more fluid to bladder (22) to create a greater degree of restriction; or increased by withdrawing fluid from bladder (22) to reduce the degree of restriction.

Figure 3:
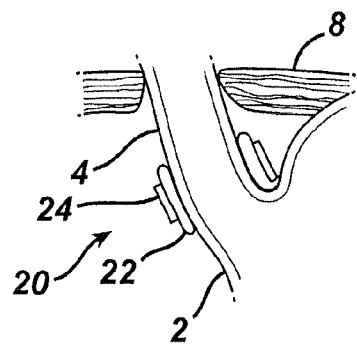
FIG. 3 depicts a cross-sectional view of the gastric band of FIG. 1, showing the band positioned around the gastro-esophageal junction of a patient in a deflated configuration.
Figure 4:
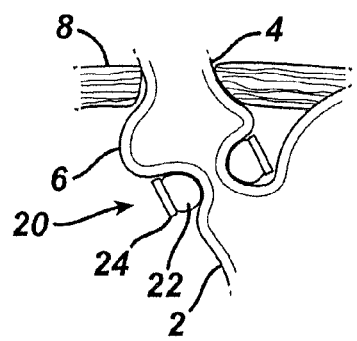
FIG. 4 depicts a cross-sectional view of the gastric band of FIG. 1, showing the band positioned around the gastro-esophageal junction of a patient in an inflated configuration to create a food intake restriction.
Figure 5:
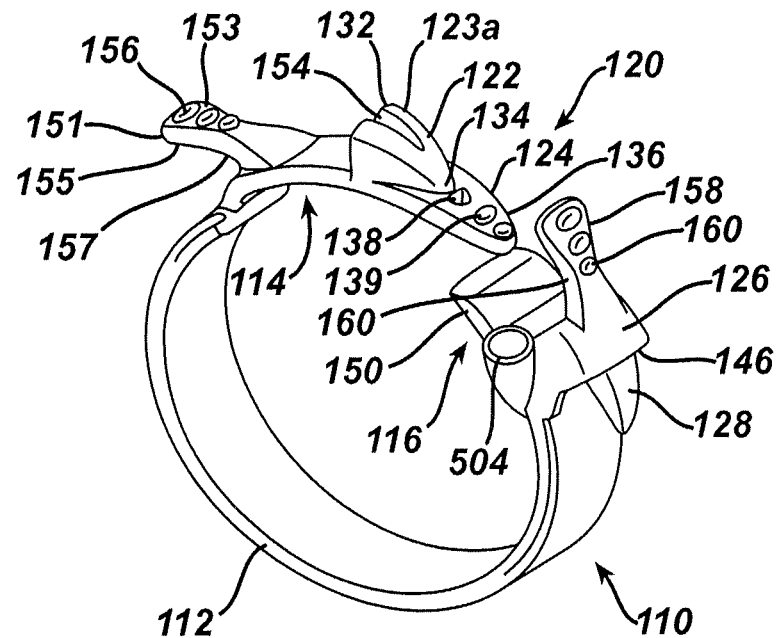
FIG. 5 depicts a first perspective view of an exemplary gastric band device.
Figure 6:
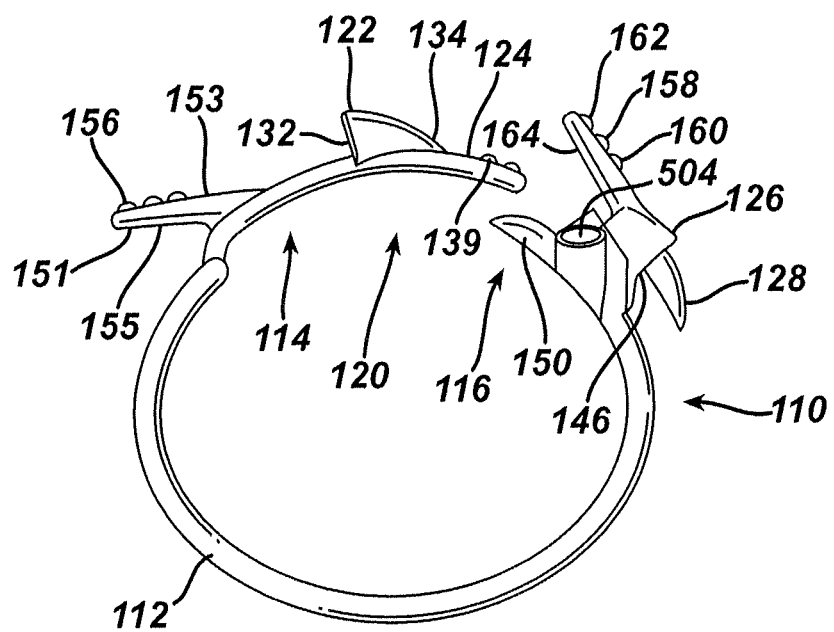
FIG. 6 depicts a side elevational view of the gastric band device of FIG. 5.
Figure 7:
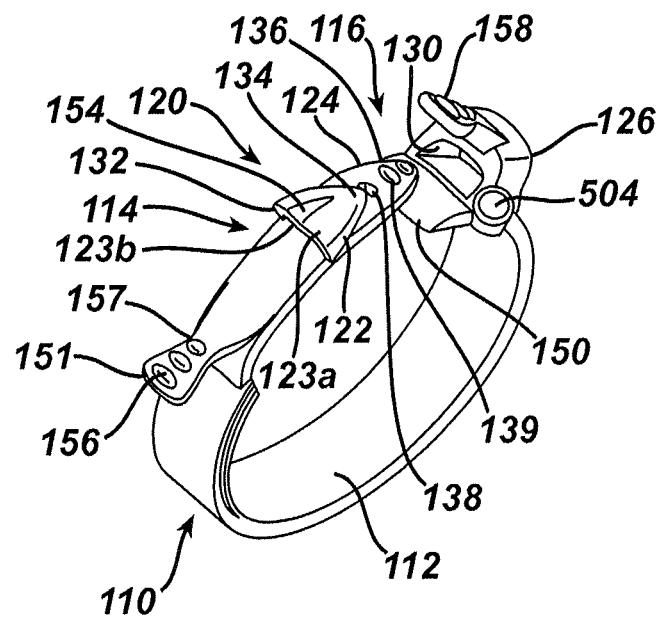
FIG. 7 depicts a second perspective view of the gastric band device of FIG. 5.
Figure 8:
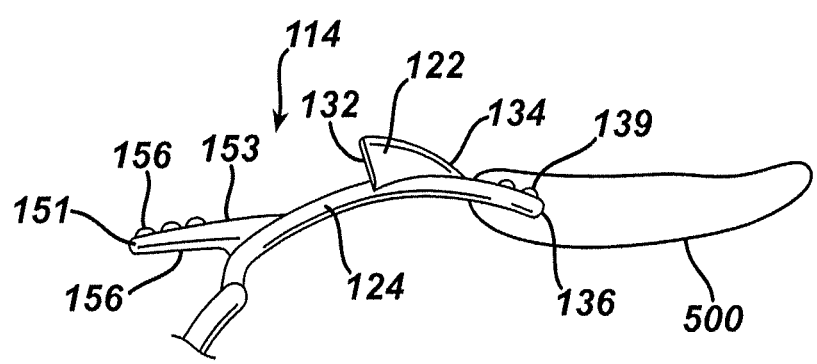
FIG. 8 depicts a partial side elevational view of an end of the gastric band device of FIG. 5.

As shown in FIGS. 2-4, an installed gastric band (20) at least substantially encloses the upper portion of stomach (2) near the junction with esophagus (4) in the present example. FIG. 3 shows gastric band (20) in a deflated configuration, where bladder (22) contains little to no fluid, thereby maximizing the size of the stoma opening into stomach (2). FIG. 4 shows gastric band (20) in an inflated, fluid-filled configuration, where bladder (22) contains substantially more fluid than is shown in FIG. 3. In this configuration shown in FIG. 4, the pressure of gastric band (20) against stomach (2) is increased due to the fluid within bladder (22), thereby decreasing the stoma opening to create a food intake restriction. FIG. 4 also schematically illustrates the dilation of esophagus (4) above gastric band (20) to form an upper pouch (6) beneath the diaphragm muscle (8) of the patient.

Exemplary Gastric Band

FIGS. 5-8 and 10B-11B show another exemplary gastric band (110), which may be easily incorporated into gastric band system of FIGS. 1-4 in place of gastric band (20). Gastric band (110) of this example includes a band body (112) having a first end (114) and a second end (116), which together form a latching mechanism (120). Band body (112) and latching mechanism (120) may be formed of silicone and/or any other suitable material or combination of materials. Like gastric band (20), gastric band (110) of the present example is shaped and dimensioned to circumscribe the stomach at a predetermined location reducing the size of the stomach. Flexible latching mechanism (120) is capable of locking and unlocking without destruction of latching mechanism (120) or significant reduction in retention capabilities after re-locking. First and second ends (114, 116) act as both male and female members depending on the direction of motion and intent to lock or unlock latching mechanism (120) of gastric band (110). Of course, gastric band (110) may alternatively latch and/or unlatch in any other suitable fashion. By way of example only, gastric band (110) may alternatively be configured such that at least a portion of gastric band (110) must be destroyed in order to remove gastric band (110) once it has been latched relative to a patient.

First end (114) includes a shell member, or first latching member (122) generally composed of a hollow, half-moon shaped shell with a tab (124) for gripping and pulling through a collar member, or second latching member (126) composed of semi-circular shaped aperture (130) on second end (116). The half-moon shell of shell member (122) collapses as it is pulled through collar member (126) as will be described in greater detail below. More particularly, shell member (122) at first end (114) of gastric band (110) is generally in the shape of a half-moon shaped shell with an open, wide end (132) tapering toward a narrow end (134) adjacent tip (136) of first end (114). Shell member (122) is substantially hollow and may be formed from a material that permits compression and expansion thereof (e.g., silicone, etc.). Shell member (122) is formed with a substantially M-shaped outer surface (123a) when viewed from the wide end (132) thereof. That is, the outer surface of shell member (122) has a substantially M-shaped profile, while the inner surface (123b) of shell member (122) adjacent wide end (132) has a substantially smooth semi-circular profile. Of course, any other suitable features and/or configurations may be used.

Collar member (126) includes a tongue (128) such that shell member (122) slides through semi-circular shaped aperture (130) and under tongue (128) during latching. In the present example, secure fastening of shell member (122) with collar member (126) is achieved by ensuring that after shell member (122) compresses while passing through collar member (126), shell member (122) returns to its original shape and wide end (132) of shell member (122) abuts with first edge (146) of collar member (126). Once shell member (122) passes tongue (128), the roles change. First end (114) functions as a female component when shell member (122) resiliently returns to its original shape and is allowed to slide back onto second end (116) (now a male component) and over tongue (128). Tongue (128) is shaped and dimensioned to seat within wide end (132) of shell member (122) after shell member (122) has passed through collar member (126) and gastric band (110) is tensioned as first and second ends (114, 116) are drawn toward each other, with shell member (122) straining to move back through collar member (126) toward an unlatched positioned. With this in mind, tongue (128) may be downwardly oriented such that it slides with shell member (122) in a convenient and reliable manner. If desired, tongue (128) may be distinctly colored to provide an indication as to whether latching mechanism (120) is properly locked.

It should be understood from the foregoing that shell member (122) of the present example functions as both a male component and female component during operation of latching mechanism (120) and collar member (126) functions as both a male component and female component during operation of latching mechanism (120). That is, shell member (122) functions as a male component during insertion through collar member (126) and a female component thereafter when tongue (128) is seated therein. Unlocking of latching mechanism (120) may be achieved by employing graspers to pull first end (114) forward away from the second end (114) removing tongue (128) from shell member (122). The M-shape of shell member (122) permits it to collapse and move under tongue (128) and through collar member (126). Of course, as with other components and features described herein, tongue (128) is merely optional and may be varied or even omitted as desired. Indeed, collar member (126) may have any other suitable features and/or configurations.

As described in greater detail below, shell member (122) is slid through collar member (126) when gastric band (110) is being installed in a patient. Thereafter, the center (154) of the M-shaped wide end (332) resiliently returns to its original shape and fits over tongue (128) in the present example. When gastric band (110) is unlatched, shell member (122) is pulled forward away from collar member (126) and M-shaped shell member (122) permits it to move under tongue (128) and through collar member (126). The preformed shape of shell member (122) not only acts as a guiding feature for tongue (128) to slide over shell member (122) during unlatching, but may also allow shell member (122) to more easily slide back through aperture (130) of collar member (126).

In the present example, an aperture (138) is formed within tab (124), adjacent tip (136) of first end (114) and the narrow end (134) of shell member (122). Aperture (138) is shaped and dimensioned for receipt of a suture, extension member or grasper commonly used in the installation of gastric bands. In particular, and as shown in FIGS. 8 and 10B-11B, a suture loop (500) is passed through aperture (138) of the present example. Ways in which suture loop (500) may be used during the installation of gastric band (110) will be described in greater detail below. It should be noted that suture loop (500) is omitted from FIGS. 5-7 for clarity. In addition to having suture loop (500) passing through aperture (138), tab (124) is formed with protrusions (139) assisting in grabbing tab (124) during manipulation of gastric band (110). Again, though, as with other components and features described herein, protrusions (139) are merely optional and may be varied or even omitted as desired.

Also at first end (114), but on the opposite side of shell member (122) from aperture (138) and adjacent wide end (132) of shell member (122), is a rearwardly extending gripping member (151). Gripping member (151) is shaped and dimensioned to permit dual directional access for locking and unlocking of latching mechanism (120). More particularly, gripping member (151) includes protrusions (156) along the top and bottom surfaces (153, 155) thereof. Protrusions (156) may facilitate gripping thereof along a first directional orientation. Gripping member (150) is further formed with an "hour glass" shaped having a reinforced central section (157). Reinforced central section (157) allows for gripping in a second directional orientation.

Gripping of second end (116) is further enhanced in the present example through the provision of a forward facing (facing tip (150) of second end (116)) gripping member (158). Forward facing gripping member (158) is shaped and dimensioned to permit dual directional access for locking and unlocking of latching mechanism (120). More particularly, gripping member (158) of this example includes protrusions (160) along the top and bottom surfaces (162, 164) thereof These protrusions (160) may facilitate gripping thereof along a first directional orientation. Gripping member (158) is further formed with an "hour glass" shape having a reinforced central section (160). Reinforced central section (160) allows for gripping in a second directional orientation. Gripping member (158) is shaped and dimensioned to receive and center shell member (122) as it passes through collar member (126). As with other components and features described herein, gripping members (151, 158) are merely optional and may be varied or even omitted as desired.

Like gastric band (20), gastric band (110) also includes an inflatable bladder (502), which is secured to the inner surface of band body (112). Bladder (502) is shown in FIGS. 10C-11B, but is omitted from FIGS. 5-8 for clarity. Band body (112) also includes a fluid port (504). Fluid port (504) is in fluid communication with bladder (502). In addition, fluid port (504) is configured to couple with a catheter (506), as shown in FIGS. 10C-11B. Fluid port (504) may thus provide fluid communication between bladder (502) and catheter (506). Catheter (506) may also be coupled with an injection port (12) as described herein. Alternatively, catheter (506) may be coupled with a pump/reservoir system. Such a pump/reservoir system may be controlled to selectively vary the amount of fluid in bladder (502). Examples of such a system are described in U.S. Pat. No. 7,390,294, entitled "Piezo Electrically Driven Bellows Infuser for Hydraulically Controlling an Adjustable Gastric Band," issued Jun. 24, 2008, the disclosure of which is incorporated by reference herein. Other examples of such a system are described in U.S. Pat. No. 7,351,240, entitled "Thermodynamically Driven Reversible Infuser Pump for Use as a Remotely Controlled Gastric Band," issued Apr. 1, 2008, the disclosure of which is incorporated by reference herein. In some other versions, gastric band (110) is modified such that it is actuated mechanically instead of hydraulically. For instance, gastric band (110) may be modified in accordance with the teachings of U.S. Pat. No. 6,067,991, entitled "Mechanical Food Intake Restriction Device," issued May 30, 2000, the disclosure of which is incorporated by reference herein. Still other suitable ways in which gastric band (110) may be modified, substituted, or supplemented will be apparent to those of ordinary skill in the art in view of the teachings herein.

Exemplary Installation Instrument

Figure 9A:
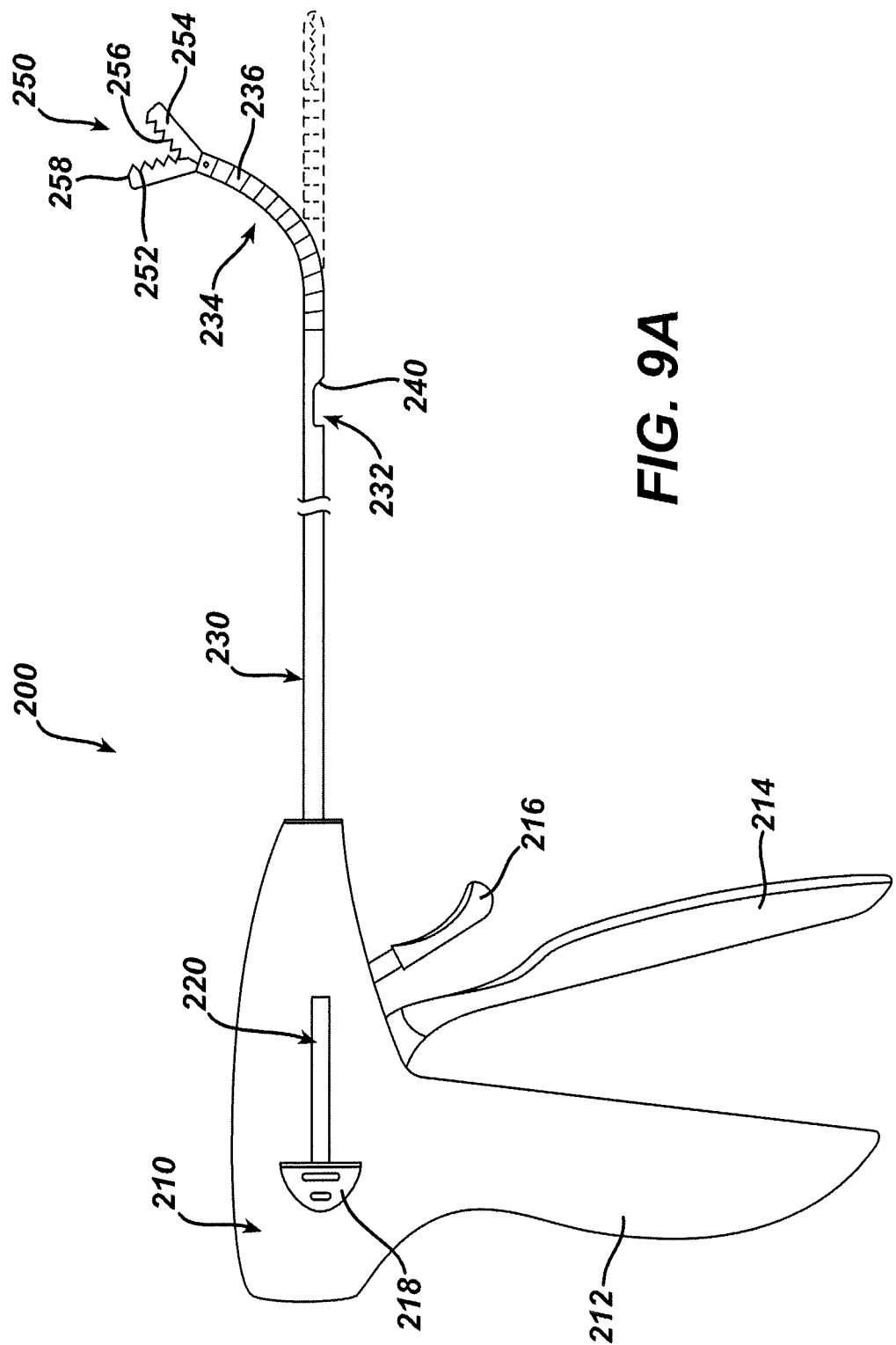
FIG. 9A depicts a side elevational view of an exemplary gastric band installation instrument, with a hook member in a retracted position.
Figure 9B:
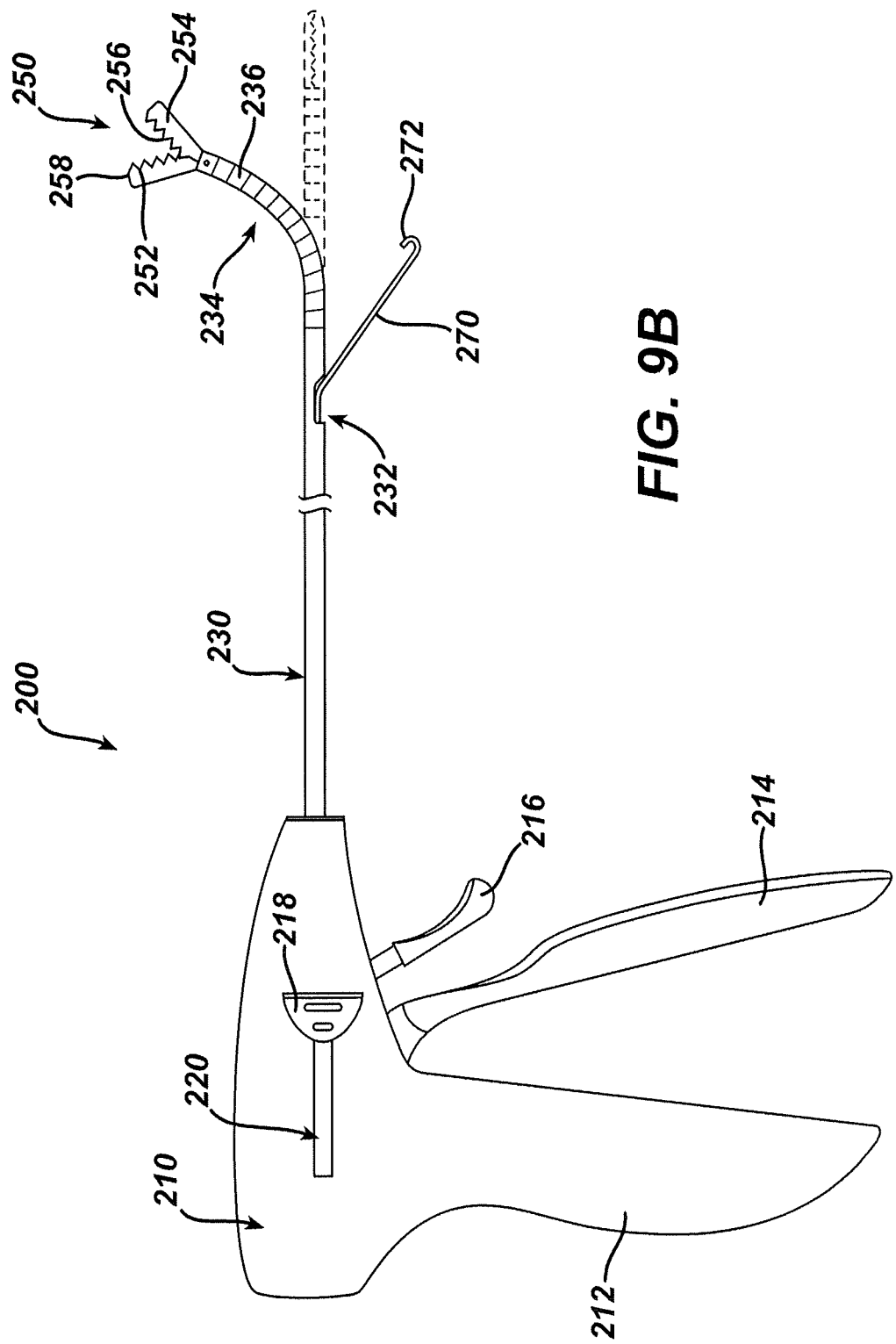
FIG. 9B depicts a side elevational view of the installation instrument of FIG. 9A, with the hook member in an extended position.

FIGS. 9A-9B show an exemplary instrument (200) that may be used to install gastric band (110). Instrument (200) of this example comprises a handle portion (210), a shaft (230), and an end effector (250). Handle portion (210) includes a pistol grip (212), a first trigger member (214), a second trigger member (216), and a slider (218). Shaft (230) includes a side aperture (232) and an articulating section (234), which is located between side aperture (232) and end effector (250). End effector (250) comprises a pair of grasping jaws (252, 254). Each of these components will be described in greater detail below.

Grasping jaws (252, 254) are configured as conventional grasping jaws, with mating serrations (256) to facilitate gripping. Of course, serrations (256) are merely optional, and may be modified, substituted, or supplemented with other structures or features, or even be omitted entirely. Each gripping jaw (252, 254) is configured to rotate toward and away from a longitudinal axis defined by shaft (230) in the present example, to selectively close or open jaws (252, 254) respectively. Alternatively, some versions may provide rotation of just one gripping jaw (252 or 254) relative to the longitudinal axis defined by shaft (230) while the other gripping jaw (254 or 254) remains substantially fixed relative to the longitudinal axis defined by shaft. In versions where each gripping jaw (252, 254) rotates toward and away from a longitudinal axis defined by shaft (230), jaws (252, 254) may rotate simultaneously or separately. In some versions, gripping jaws (252, 254) are resiliently biased to assume an open position, whereby jaws (252, 254) are separated from each other as shown with solid lines in FIGS. 9A-9B. In some other versions, gripping jaws (252, 254) are resiliently biased to assume a closed position, whereby jaws (252, 254) are adjacent to each other along their full lengths as shown with broken lines in FIGS. 9A-9B. Alternatively, gripping jaws (252, 254) may be configured such that they are neither resiliently biased to an open position nor resiliently biased to a closed position.

In the present example, jaws (252, 254) are actuated by second trigger member (216). In particular, a user may squeeze second trigger member (216) toward pistol grip (212) to urge gripping jaws (252, 254) toward each other to the closed position. Second trigger member (216) is resiliently biased to rotate away from pistol grip (212), such that jaws (252, 254) are resiliently biased toward the open position. For instance, a spring or other type of device within handle portion (210) may provide such a resilient bias to second trigger member (216). In some other versions, instrument (200) is configured such that jaws (252, 254) are resiliently biased toward the open position; and such that squeezing second trigger member (216) toward pistol grip (212) urges gripping jaws (252, 254) away from each other to the open position.

It should also be understood that second trigger member (216) may be coupled with jaws (252, 254) to selectively actuate jaws (252, 254) in a variety of ways. By way of example only, instrument (200) may include a rack and pinion in handle portion (210), one or more push/pull cables or rods in shaft (230), and/or a variety of other types of components to couple second trigger member (216) with jaws (252, 254). Various suitable components and configurations that may be used to couple second trigger member (216) with jaws (252, 254) will be apparent to those of ordinary skill in the art in view of the teachings herein. It should also be understood that instrument (200) may include one or more locking features for jaws (252, 254) and/or second trigger member (216). For instance, a locking feature may selectively lock jaws (252, 254) to the closed position (e.g., by locking the rotational position of second trigger member (216) relative to pistol grip (212), etc.). Various forms that such optional locking features may take will be apparent to those of ordinary skill in the art in view of the teachings herein.

While jaws (252, 254) are shown as opening and closing along a vertical plane, jaws (252, 254) may instead open and close along a horizontal plane (e.g., such that jaws (252, 254) are both rotated 90° about the longitudinal axis defined by shaft (230) relative to the configuration shown in FIGS. 9A-9B, etc.). In some versions, instrument (200) is further operable to rotate jaws (252, 254) about the longitudinal axis defined by shaft (230). For instance, instrument (200) may include a knob, dial, other type of rotatable member, or other feature that is operable to rotate jaws (252, 254) about the longitudinal axis defined by shaft (230). Furthermore, such rotation of jaws (252, 254) may be relative to shaft (230), such that shaft (230) remains substantially stationary as jaws (252, 254) rotate about the longitudinal axis defined by shaft (230). In some other versions, shaft (230) rotates about its own longitudinal axis, relative to handle portion (210). In some such versions, jaws (252, 254) and/or articulating section (234) may rotate concomitantly with shaft (230). Alternatively, these components may rotate independently relative to each other. Of course, such components may simply not be rotatable at all in some versions of instrument (200).

Articulation section (234) of the present example comprises a plurality of segments (236) that are configured to permit selective deflection of end effector (250) away from and back toward the longitudinal axis defined by shaft (230).

In some versions, articulation section (234) is resiliently biased to assume an articulated position, whereby articulation section (234) is deflected as shown with solid lines in FIGS. 9A-9B. In some other versions, articulation section (234) is resiliently biased to assume a non-articulated position, whereby articulation section (234) is substantially coaxial with shaft (230) as shown with broken lines in FIGS. 9A-9B. Alternatively, articulation section (234) may be configured such that it is neither resiliently biased to an articulated position nor resiliently biased to a non-articulated position. In addition, while articulation section (234) is shown as being deflected upwardly in FIGS. 9A-9B, it should be understood that articulation section (234) may be deflectable downwardly, sideways, or in any other suitable direction, in addition to being deflectable upwardly. In other words, articulation section (234) may articulate along just one plane of articulation in some versions; while articulation section (234) may articulate along more than one plane of articulation in some other versions.

In the present example, articulation section (234) is actuated by first trigger member (214). In particular, a user may squeeze first trigger member (216) toward pistol grip (212) to urge articulation section (234) to the articulated position. First trigger member (214) is resiliently biased to rotate away from pistol grip (212), such that articulation section (234) is resiliently biased toward the non-articulated position. For instance, a spring or other type of device within handle portion (210) may provide such a resilient bias to first trigger member (214). In some other versions, instrument (200) is configured such that articulation section (234) is resiliently biased toward an articulated position; and such that squeezing first trigger member (214) toward pistol grip (212) urges articulation section to a non-articulated position.

It should be understood that articulation section (234) may have a variety of components, features, and configurations. By way of example only, articulation section (234) may be configured in accordance with the teachings of U.S. Pub. No. 2007/0185518, entitled "Method for Aiding a Surgical Procedure," published Aug. 9, 2007, the disclosure of which is incorporated by reference herein. As another merely illustrative example, articulation section (234) may be configured in accordance with the teachings of U.S. Pub. No. 2007/0288048, entitled "Articulating Blunt Dissector/Gastric Band Application Device," published Dec. 13, 2007, the disclosure of which is incorporated by reference herein. As yet another merely illustrative example, articulation section (234) may be configured in accordance with the teachings of U.S. Pat. No. 5,522,788, entitled "Finger-Like Laparoscopic Blunt Dissector Device," issued Jun. 4, 1996, the disclosure of which is incorporated by reference herein. Still other suitable components, features, and configurations for articulation section (234) will be apparent to those of ordinary skill in the art in view of the teachings herein. In addition, while articulation section (234) is shown as flexing between a non-articulated position and an articulated position where articulation section (234) follows a simple single curve, articulation section (234) may be configured to articulate along multiple curves or complex curves (e.g., such that articulation section (234) forms an "S"-like configuration, etc.). In some versions, articulation section (234) may simply be omitted if desired.

It should also be understood that first trigger member (214) may be coupled with articulation section (234) to selectively actuate articulation section (234) in a variety of ways. By way of example only, instrument (200) may include a rack and pinion in handle portion (210), one or more push/pull cables or rods in shaft (230), and/or a variety of other types of components to couple first trigger member (214) with articulation section (234). In some versions, first trigger member (214) is coupled with articulation section (234) in accordance with the teachings of U.S. Pub. No. 2007/0185518, entitled "Method for Aiding a Surgical Procedure," published Aug. 9, 2007, the disclosure of which is incorporated by reference herein. In some other versions, first trigger member (214) is coupled with articulation section (234) in accordance with the teachings of U.S. Pub. No. 2007/0288048, entitled "Articulating Blunt Dissector/Gastric Band Application Device," published Dec. 13, 2007, the disclosure of which is incorporated by reference herein. Still other suitable components and configurations that may be used to couple first trigger member (214) with articulation section (234) will be apparent to those of ordinary skill in the art in view of the teachings herein. Likewise, various ways in which actuation components for jaws (252, 254) and actuation components for articulation section (234) may suitably fit together within shaft (230) will be apparent to those of ordinary skill in the art in view of the teachings herein.

It should also be understood that instrument (200) may include one or more locking features for articulation section (234) and/or first trigger member (214). For instance, a locking feature may selectively lock articulation section (234) to a selected articulation position (e.g., by locking the rotational position of first trigger member (214) relative to pistol grip (212), etc.). Various forms that such optional locking features may take will be apparent to those of ordinary skill in the art in view of the teachings herein. Of course, like other features described herein, articulation section (234) is merely optional. For instance, some versions of instrument (200) may have a substantially rigid, non-articulating shaft (230) (e.g., one that completely lacks an articulation section (234), etc).

Figure 11A:
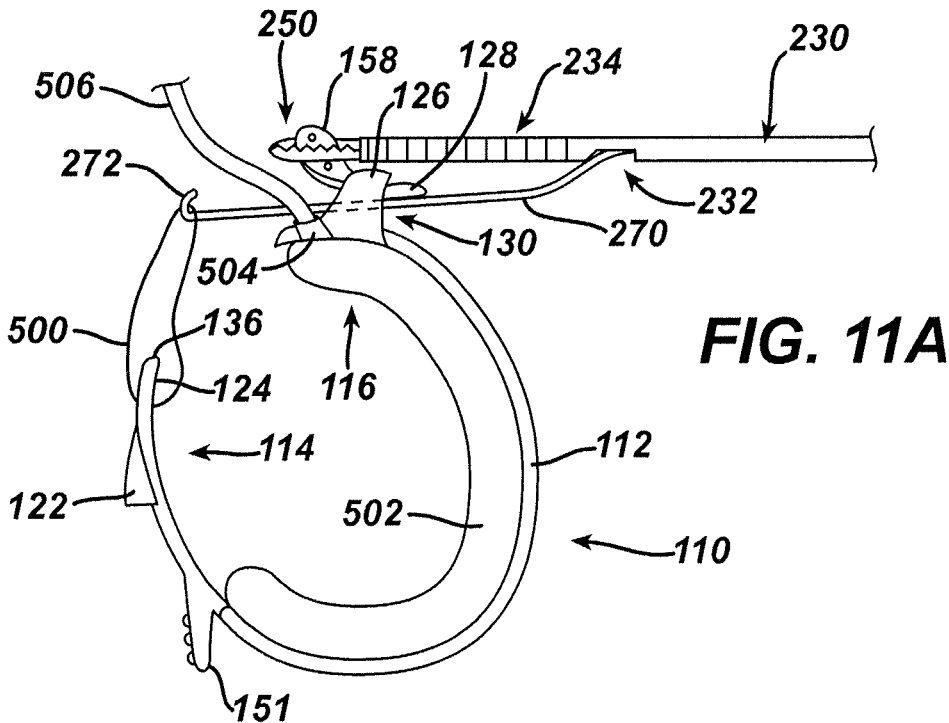
FIG. 11A depicts a partial side view of the installation instrument of FIG. 9A and the gastric band device of FIG. 5, with the hook member of the installation device in an extended position to capture the suture loop of the gastric band device.
Figure 11B:
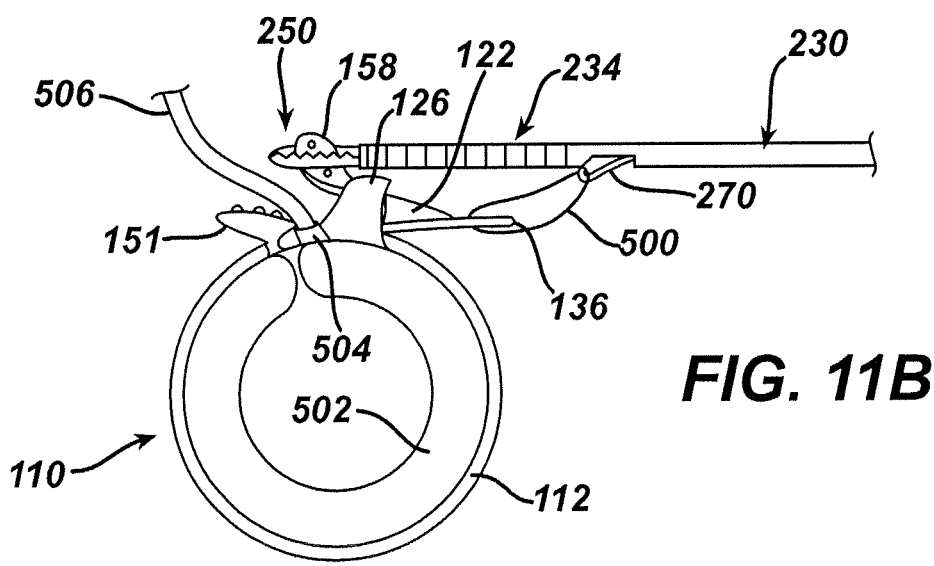
FIG. 11B depicts a partial side view of the installation instrument of FIG. 9A and the gastric band device of FIG. 5, with the hook member of the installation device in a retracted position to latch the ends of the gastric band device together.

Instrument (200) of the present example also includes a hook member (270), as shown in FIGS. 9B and 11A-11B. Hook member (270) extends through shaft (230). In particular, hook member (270) terminates in a hook portion (272) at its distal end and is translationally coupled with slider (218) at its proximal end. Hook member (270) may comprise a wire or a strip of band-like material. By way of example only hook member (270) may be formed of metal, such as nitinol. Alternatively, hook member (270) may be formed of any other suitable material or combination of materials. In the present example, hook member (270) is resilient. In particular, hook member (270) is resiliently biased to assume a substantially straight configuration (e.g., parallel to the longitudinal axis defined by shaft (230), etc.). To the extent that hook member (270) is resilient, hook member (270) need not necessarily be resiliently biased to assume a substantially straight configuration. For instance, hook member (270) may be resiliently biased to assume a curved configuration, a bent configuration, or some other type of configuration. Of course, hook member (270) may have any other suitable properties, in addition to or in lieu of being resilient. It should also be understood that hook member (270) may be substituted with a translating grasper device (e.g., such that hook portion (272) is substituted with grasping jaws, etc.).

Slider (218) is translatable along slot (220) formed in handle portion (210), to selectively extend or retract hook member (270) from side aperture (232) of shaft (230). In the present example, the coupling of hook member (270) with slider (218) is such that hook member (270) and slider (218) translate unitarily relative to shaft (230) (e.g., such that the translation distance is the same for hook member (270) and slider (218), etc.). In some versions, the coupling of hook member (270) with slider (218) translation of slider (218) along a relatively small distance produces translation of hook member (270) along a relatively greater distance. Of course, slider (218) and hook member (270) may be coupled in a variety of ways, and a variety of other structures or features may be used to supplement or substitute slider (218).

FIG. 9A shows instrument (200) with slider (218) in a proximal position along slot (220); and with hook member (270) retracted within shaft (230). In this example, hook portion (272) is fully retracted within shaft (230), such that hook portion (272) is proximal to the proximal edge of side aperture (232). In some other versions, hook portion (272) is longitudinally co-located with side aperture (232) when hook member (270) is in the retracted position, such that hook portion (272) would still be visible through side aperture (232) in the view shown in FIG. 9A, yet such that hook portion (272) does not extend radially outwardly past the outer perimeter of shaft (230).

FIG. 9B shows instrument (200) with slider (218) in a distal position along slot (220); and with hook member (270) extended relative to shaft (230). In particular, hook member (270) protrudes through side aperture (232), presenting hook portion (272) outside of shaft (230). Shaft (230) includes a ramped surface (240) that is configured to promote protrusion of hook member (270) through side aperture (232) when hook member (270) is advanced distally by slider (218). In addition to or in lieu of having ramped surface (240), the configuration and/or properties of hook member (270) may promote protrusion of hook member (270) through side aperture (232) when hook member (270) is advanced distally by slider (218). As noted above, hook member (270) is resiliently biased to assume a substantially straight configuration (e.g., parallel to the longitudinal axis defined by shaft (230), etc.) in the present example. Thus, in some versions, the portion of hook member (270) that is exposed through side aperture (232) may become more parallel with shaft (230) as hook member (270) is extended further through side aperture (232). In other words, the degree of deflection of hook member (270) relative to shaft (230) shown in FIG. 9B may be greater than the actual degree of deflection of hook member (270) relative to shaft (230) in some versions.

Similarly, slider (218), slot (220), hook member (270), and shaft (230) may be configured such that hook member (270) extends to any suitable longitudinal distance. In particular, slider (218), slot (220), hook member (270), and shaft (230) may be configured such that hook portion (272) of hook member (270) extends distally past the tips (258) of jaws (252, 254) when hook member (270) is at a fully extended position (even with jaws (252, 254) closed and with articulation section (234) in a non-articulated position). In other words, the actual degree of longitudinal extension of hook member (270) may be greater in some versions than the degree of longitudinal extension of hook member (270) shown in FIG. 9B. Suitable degrees to which hook member (270) may longitudinally extend relative to shaft (230) and end effector (250), etc., will be apparent to those of ordinary skill in the art in view of the teachings herein.

While hook portion (272) of hook member (270) is shown in FIG. 9B as being oriented upwardly, it should be understood that hook portion (272) of hook member (270) may have any other suitable orientation. By way of example only, hook portion (272) may alternatively be oriented downwardly, sideways, or otherwise. Furthermore, some versions of instrument (200) may be operable to rotate hook member (270) about the longitudinal axis defined by shaft (230) (e.g., to re-orient hook portion (272), etc.). For instance, instrument (200) may include a knob, dial, other type of rotatable member, or other feature that is operable to rotate hook member (270) about the longitudinal axis defined by shaft (230). Furthermore, such rotation of hook member (270) may be relative to shaft (230), such that shaft (230) remains substantially stationary as hook member (270) rotates about the longitudinal axis defined by shaft (230). As another merely illustrative variation, hook member (270) and shaft (230) may rotate together, relative to handle portion (210). In some such versions, jaws (252, 254) may remain substantially stationary as hook member (270) and shaft (230) rotate together relative to handle portion (210). Such rotation of hook member (270) with shaft (230) may be provided in addition to or in lieu of providing rotatability of hook member (270) independent of shaft (230) rotation. It should also be understood that instrument (200) may include one or more locking features for slider (218) and/or hook member (270). For instance, a locking feature may selectively lock hook member (270) to a longitudinally extended position (e.g., by locking the translational position of slider (218), etc.). Various forms that such optional locking features may take will be apparent to those of ordinary skill in the art in view of the teachings herein. In addition, various suitable ways in which hook member (270), actuation components for jaws (252, 254), and actuation components for articulation section (234) may fit together within shaft (230) will be apparent to those of ordinary skill in the art in view of the teachings herein.

Those of ordinary skill in the art should appreciate that the illustrated configuration of handle portion (210) is merely exemplary. For instance, handle portion (210) may have a scissor grip configuration instead of a pistol grip configuration. Alternatively, handle portion (210) may be configured like the handle portion in U.S. Pub. No. 2007/0185518, entitled "Method for Aiding a Surgical Procedure," published Aug. 9, 2007, the disclosure of which is incorporated by reference herein. As yet another merely illustrative alternative, handle portion (210) may be configured like the handle portion in U.S. Pub. No. 2007/0288048, entitled "Articulating Blunt Dissector/Gastric Band Application Device," published Dec. 13, 2007, the disclosure of which is incorporated by reference herein. Similarly, it should be understood that any or all of first trigger member (214), second trigger member (216), and/or slider (218) may be substituted with a variety of other types of actuators. It should also be understood that articulating section (234), end effector (250), and/or hook member (270) may be actuated electrically (e.g., by electroactive polymers, etc.), electromechanically (e.g., by solenoids, motors, etc.), pneumatically, hydraulically, and/or in any other suitable fashion. Still other suitable components, features, configurations, and functionalities of handle portion (210) and any other part of instrument (200) will be apparent to those of ordinary skill in the art in view of the teachings herein.

Exemplary Installation of Gastric Band

Figure 10A:
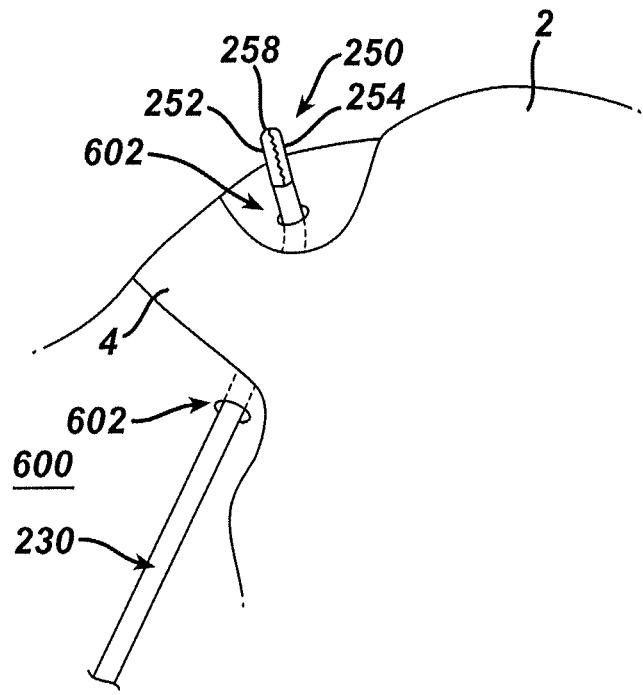
FIG. 10A depicts a partial view of the installation instrument of FIG. 9A having tunneled through tissue near a patient's stomach.

FIGS. 10A-11B illustrate various exemplary steps that may be taken to use instrument (200) to install gastric band (110). In particular, FIGS. 10A-10C illustrate exemplary steps whereby instrument (200) is used to position gastric band (110); while FIGS. 11A-11B illustrate exemplary steps whereby instrument (200) is used to secure gastric band (110). These steps will be described in greater detail below. However, it should be understood that these steps are merely exemplary, and that instrument (200) and/or gastric band (110) may be used in a variety of other ways as will be apparent to those of ordinary skill in the art in view of the teachings herein.

Instrument (200) is introduced into the patient's body through a trocar or other type of port (e.g., a multi-port trocar, etc.). By way of example only, instrument (200) may be introduced into the patient's body through a port configured in accordance with the teachings of U.S. application Ser. No. 12/512,542, entitled "Methods and Devices for Providing Access into a Body Cavity," filed Jul. 30, 2009, now U.S. Pub. No. 2011/0028793, published Feb. 3, 2011, the disclosure of which is incorporated by reference herein. One or more additional types of surgical instruments (e.g., conventional surgical graspers, etc.) may also be introduced into the patient's body to further assist in the installation of gastric band (110), as will be described in greater detail below.

Once instrument (200) has been introduced into the patient's body, instrument (200) is used to form a retrogastric tunnel (602) through tissue (600) that is adjacent to the patient's stomach (2) and esophagus (4). In particular, with jaws (252, 254) in a closed position, tips (258) of closed jaws (252, 254) are used to perform blunt dissection through tissue (600) to form tunnel (602) as shown in FIG. 10A. Of course, some type of bladed cutting device, an electrosurgical device, or some other type of device may be used to start or otherwise form tunnel (602), if desired. As is also shown in FIG. 10A, shaft (230) enters one side of tunnel (602) while jaws (252, 254) are exposed through the other end of tunnel (602). It should be understood that the user may manipulate articulating section (234) before, during, and/or after the creation of tunnel (602). Next, gastric band (110) is introduced into the patient's body. It should be understood that gastric band (110) may be introduced through a trocar or other type of port as described above, using conventional surgical graspers or some other type of device.

Figure 10B:
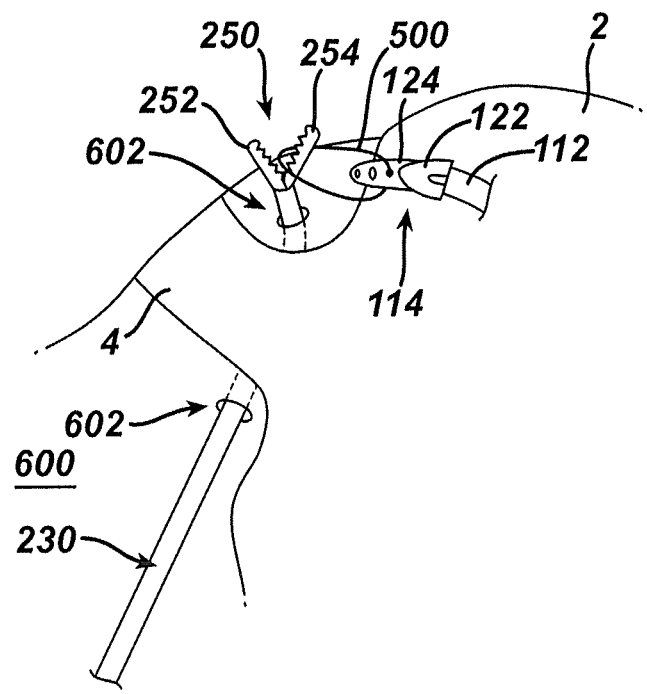
FIG. 10B depicts a partial view of the installation instrument of FIG. 9A with its graspers receiving a suture loop of the gastric band device of FIG. 5.

Gastric band (110) is then positioned near jaws (252, 254) of instrument (200), as shown in FIG. 10B. FIG. 10B just shows first end (114) of gastric band (110), though it should be understood that the entirety of gastric band (110) may be positioned within the patient at this time. Jaws (252, 254) are opened to receive suture loop (500), as also shown in FIG. 10B. It should be understood that the user may manipulate articulating section (234) to reach for suture loop (500) with jaws (252, 254) or to otherwise facilitate placement of suture loop (500) in open jaws (252, 254). It should also be understood that one or more other devices (e.g., conventional graspers, etc.) may be used to assist in placement of suture loop (500) in open jaws (252, 254). Once suture loop (500) has been placed in open jaws (252, 254), jaws (252, 254) are clamped down on suture loop (500) to the closed position. In some versions, tab (124) or some other part of gastric band (110) is placed in open jaws (252, 254) and then clamped down on by jaws (252, 254).

Figure 10C:
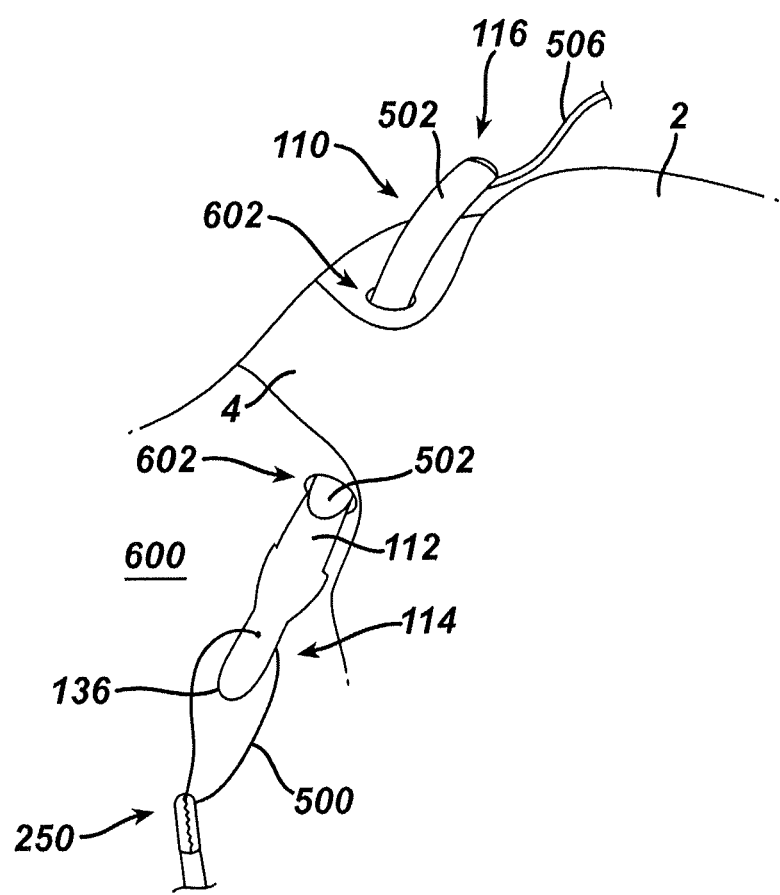
FIG. 10C depicts a partial view of the installation instrument of FIG. 9A having pulled the gastric band device of FIG. 5 through the tunnel of FIG. 10A.

With suture loop (500) (or some other part of gastric band (110)) clamped in closed jaws (252, 254), shaft (230) is then pulled back through tunnel (602) to pull gastric band (110) through tunnel (602). In particular, and as shown in FIG. 10C, instrument (200) is used to pull gastric band (110) through tunnel (602) to a position where first end (114) of gastric band (110) protrudes from one end of tunnel (602) while second end (116) of gastric band (110) protrudes from the other end of tunnel (602). Pulling gastric band (110) through tunnel (602) may or may not widen tunnel (602) to some degree. At this stage, instrument (200) and/or one or more additional instruments (e.g., conventional graspers, etc.) is/are used to wrap gastric band (110) around the gastro-esophageal junction of the patient, by bringing first and second ends (114, 116) of gastric band (110) toward each other. In particular, gastric band (110) is manipulated to the position shown in FIG. 11A. Parts of the human anatomy are omitted from FIGS. 11A-11B for clarity, though it should be understood that gastric band (110) may be positioned about the gastroesophageal junction of the patient and be inserted through tunnel (602) at the procedural stages illustrated in FIGS. 11A-11B.

As shown in FIG. 11A, jaws (252, 254) are used to grasp gripping member (158) of gastric band (110). Jaws (252, 254) thereby hold second end (116) of gastric band (110) in place. With gripping member (158) being securely held by jaws (252, 254), hook member (270) is extended distally from side aperture (232). As noted above, slider (218) may be used to advance hook member (270) from a proximally retracted position to a distally extended position. As part of this distal extension, hook member (270) is extended through aperture (130) of collar member (126), beneath gripping member (158) and tongue (128). Hook member (270) is extended distally to a point where hook portion (272) of hook member (270) may receive suture loop (500) as shown in FIG. 11A. It should be understood that one or more other instruments (e.g., conventional graspers, etc.) may be used to facilitate placement of suture loop (500) in hook portion (272). It should also be understood that articulating section (234) may be manipulated to facilitate placement of suture loop (500) in hook portion (272).

With suture loop (500) being suitably received in hook portion (272) of hook member (270), hook member (270) is then proximally retracted to pull suture loop (500) and parts of first end (114) of gastric band (110) through aperture (130) of collar member (126) as shown in FIG. 11B. As noted above, slider (218) may be used to withdraw hook member (270) from a distally extended position to a proximally retracted position. With hook member (270) sufficiently retracted, first end (114) of gastric band (110) is pulled through aperture (130) of collar member (126) to a degree sufficient to allow full passage of shell member (122) through aperture of collar member (126); and to allow tongue (128) to seat within wide end (132) of shell member (122) as described above. Gastric band (110) is thus sufficiently latched at this stage. Jaws (252, 254) may then release gripping member (158) and hook portion (272) may then release suture loop (500). In some versions, upon successful latching of latching mechanism (120), hook member (270) is again advanced distally (albeit slightly) in order to disengage suture loop (500) from hook portion (272) before hook member (270) is moved proximally a second time to retract fully back into shaft (230). Alternatively, suture loop (500) may be severed to disengage hook portion (272). With instrument (200) thus being disengaged from installed gastric band (110), and with hook member (270) being fully withdrawn into shaft (230), shaft (230) of instrument (200) may then be withdrawn from the patient. Fluid may be added to bladder (502) via catheter (506) using any suitable devices and techniques, including but not limited to those described herein, to form a restrictive stoma within the patient's stomach (2) and/or esophagus (4).

It should be understood that the distance between end effector (250) and side aperture (232), as well as the length and stroke of hook member (270), may be selected to provide complete latching of latching mechanism (120) upon full retraction of hook member (270) while jaws (252, 254) grasp gripping member (158) and while hook portion (272) engages suture loop (500). In addition, these components of instrument (200) may be configured such that complete latching of latching mechanism (120) is provided upon proximal retraction of hook member (270) to any desired distance. For instance, these components of instrument (200) may be configured such that complete latching of latching mechanism (120) is provided upon proximal retraction of hook member (270) to a position where hook portion (272) is still distal to side aperture (232). As another merely illustrative example, these components of instrument (200) may be configured such that complete latching of latching mechanism (120) is provided upon proximal retraction of hook member (270) to a position where hook portion (272) is retracted into or at least adjacent to side aperture (232). It should be understood from the foregoing that instrument (200) may be used by itself to complete latching of a gastric band (110). In other words, some versions of instrument (200) provide latching of a gastric band (200) with a single device, such that additional devices (e.g., additional graspers) are not needed to complete latching of latching mechanism (120) of gastric band (110).

In some settings, the user may manipulate articulating section (234) to assist in positioning first end (114) relative to second end (116) to effect sufficient latching of latching mechanism (120). For instance, articulating section (234) may be manipulated to change the effective length between hook portion (272) and jaws (252, 254) while jaws (252, 254) grasp gripping member (158) and while suture loop (500) is disposed in hook portion (272). Still other suitable ways in which instrument (200) may be used to position and/or secure gastric band (110) within a patient will be apparent to those of ordinary skill in the art in view of the teachings herein. By way of example only, some alternative techniques may include using a first instrument (e.g., the GOLDFINGER device by Ethicon Endo-Surgey of Cincinnati, Ohio) to perform the steps shown in FIGS. 10A-10C; and using instrument (200) to perform the steps shown in FIGS. 11A-11B.

It will become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Versions of the present invention have application in conventional endoscopic and open surgical instrumentation as well as application in robotic-assisted surgery.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a handle;
   (b) a shaft extending from the handle, wherein the shaft has a proximal end and a distal end, wherein the shaft comprises:
      (i) a rigid proximal portion having a hollow interior,
      (ii) an articulatable distal portion extending from a distal end of the rigid proximal portion, and
      (iii) a first translating member slidably disposed within the hollow interior of the rigid proximal portion, wherein the first translating member is configured to translate within the shaft to thereby cause articulation of the articulatable distal portion, wherein the shaft defines a side aperture in the rigid proximal portion, wherein the proximal end of the shaft is secured to the handle;
   (c) an end effector integrally affixed to a distal end of the articulatable distal portion of the shaft, wherein the end effector comprises a first engagement feature operable to engage a first part of a gastric band;
   (d) a second translating member slidably disposed within the hollow interior of the rigid proximal portion of the shaft, wherein the second translating member is translatable relative to the distal articulatable portion and the end effector, wherein the second translating member comprises a second engagement feature operable to engage a second part of a gastric band while the first engagement feature engages the first part of the gastric band;
   (e) a guidance feature formed in the side aperture and extending partially across the hollow interior of the rigid proximal portion of the shaft, wherein the guidance feature is configured to guide said second engagement feature out of the side aperture of the shaft and obliquely away from a longitudinal axis of the rigid proximal portion of the shaft to a first position as said second translating member is moved to a first distal position, wherein the second translating member is resiliently biased, and wherein the resilient bias is configured either to drive the second engagement feature away from the longitudinal axis of the rigid proximal portion of the shaft or to drive the second engagement feature toward the longitudinal axis of the rigid proximal portion of the shaft to a second position as the second translating member is moved further distally to a second distal position; and
   (f) a gastric band, wherein the gastric band has a first end and a second end, wherein the first end of the gastric band and the second end of the gastric band together define a latching mechanism, wherein the end effector is configured to engage and stabilize the first end, wherein the guidance feature is configured to guide the second translating member through a portion of the first end as the second translating member is driven from the first distal position to the second distal position, wherein the second translating member is further operable to engage and grasp the second end of the gastric band in the second distal position, and wherein the second end of the gastric band is operable to latch with the first end of the gastric band as the second translating member is driven from the second distal position to the first distal position while the end effector stabilizes the first end;
   wherein the articulatable distal portion is configured to articulate to thereby position the first engagement feature relative to the second engagement feature, and wherein the articulatable distal portion is further configured to articulate to thereby position the first engagement feature without changing a position of the second engagement feature.

2. The apparatus of claim 1, wherein the second translating member comprises an elongate hook member extending distally from the handle, wherein the second engagement feature comprises a hook portion curving back toward the handle.

3. The apparatus of claim 2, wherein the hook member is formed of a band of resilient metal.

4. The apparatus of claim 1, wherein the side aperture opens transversely relative to the longitudinal axis of the rigid proximal portion of the shaft.

5. The apparatus of claim 4, wherein the guidance feature comprises a ramp at a distal portion of the side aperture, wherein the ramp is configured to guide the second translating member out of and away from the shaft and through the side aperture as the second translating member is moved distally.

6. The apparatus of claim 4, wherein the distal articulatable portion is further operable to articulate the shaft along one or more planes of articulation.

7. The apparatus of claim 1, wherein the first engagement feature comprises a pair of grasping jaws movable between open and closed positions.

8. The apparatus of claim 7, wherein the grasping jaws have tips configured to perform blunt dissection of tissue when the jaws are in the closed position.

9. The apparatus of claim 1, wherein the handle comprises a pistol grip portion.

10. The apparatus of claim 9, wherein the handle comprises a first trigger member pivotable toward and away from the pistol grip portion to selectively actuate the end effector.

11. The apparatus of claim 1, wherein the handle comprises a slider coupled with the second translating member, wherein the slider is operable to translate the second translating member relative to the shaft.

12. An apparatus, comprising:
(a) a handle;
(b) a shaft extending from the handle, wherein the shaft comprises:
  (i) a rigid proximal portion having a hollow interior,
  (ii) an articulatable distal portion extending from a distal end of the rigid proximal portion, and
  (iii) a translating member configured to translate within the shaft to thereby cause articulation of the articulatable distal portion, wherein the rigid proximal portion of the shaft defines a side aperture, wherein the shaft has a proximal end and a distal end, wherein the proximal end of the shaft is secured to the handle;
(c) an end effector integrally affixed to a distal end of the articulatable distal portion of the shaft, wherein the end effector comprises a pair of grasping jaws;
(d) a hook member positioned within the shaft translatable relative to the shaft, wherein the hook member comprises a hook portion operable to engage a second part of a gastric band while the grasping jaws grasp the first part of the gastric band, wherein the hook member is rotatable, wherein the hook member is resiliently biased to have either a curved configuration or a bent configuration, and wherein the resilient bias is configured to initially drive the hook member obliquely away from a longitudinal axis defined by the rigid proximal portion of the shaft;
(e) a guidance feature formed in the side aperture and extending partially across the hollow interior of the rigid proximal portion of the shaft, wherein the guidance feature is configured to guide said hook member through the side aperture of the shaft and obliquely away from the shaft as said hook member is moved to a distal position; and
(f) a gastric band, wherein the gastric band has a first end and a second end, wherein the first end of the gastric band and the second end of the gastric band together define a latching mechanism, wherein the grasping jaws of the end effector are operable to grasp and stabilize the first end, wherein the hook member is configured to pass through a portion of the first end as the hook member is driven from a first distal position to a second distal position, wherein the hook member is operable to engage a looping feature of the second end of the gastric band in the second distal position, and wherein the second end of the gastric band is operable to latch with the first end of the gastric band as the hook member is driven from the second distal position to the first distal position while the grasping jaws stabilize the first end;
wherein the articulatable distal portion is configured to articulate to thereby position the grasping jaws relative to the hook member, and wherein the articulatable distal portion is further configured to articulate to thereby position the grasping jaws independently of the hook member.

13. The apparatus of claim 12, wherein the side aperture opens transversely relative to the longitudinal axis defined by the rigid proximal portion of the shaft, wherein the hook member is configured to selectively protrude through the side aperture when the hook member is moved to a distal position to expose the hook portion, wherein the side aperture is proximal to the end effector.

14. The apparatus of claim 13, wherein the articulatable distal portion is operable to articulate the end effector along one or more planes of articulation.

15. The apparatus of claim 12, wherein the hook member is movable from a distal position to a proximal position while the end effector remains at a substantially fixed position as the grasping jaws grasp the first part of the gastric band, to move the second part of the gastric band proximally while the first part of the gastric band is held in a substantially fixed position by the end effector.

16. A method of using an instrument to install a gastric band, wherein the gastric band has a first end and a second end, wherein the first end of the gastric band and the second end of the gastric band together define a latching mechanism, wherein the instrument comprises a grasping end effector integrally affixed to a distal end of an articulation section of a shaft, a rotatable hook member having a resilient bias positioned within the shaft and which is translatable relative to the shaft, and a guidance feature configured to guide the hook member out of the shaft, the method comprising:
(a) positioning the grasping end effector relative to the hook member by articulating the articulation section, wherein the hook member remains stationary as the articulation section is articulated,
(b) grasping the first end of the gastric band with the grasping end effector;
(c) translating the hook member in a first direction relative to the grasping end effector, thereby guiding the hook member out of the shaft to engage the second end of the gastric band with the hook member, wherein guiding the hook member to engage the second end of the band comprises adjusting the longitudinal position of the hook member in order to utilize the resilient bias of the hook member to thereby drive the hook member through the first end of the gastric band and toward second end of the gastric band, wherein the grasping end effector remains stationary as the hook member is translated in the first direction; and
(d) translating the hook member in a second direction relative to the grasping end effector to pull the second end of the gastric band toward the first end of the gastric band to latch the latching mechanism, wherein the first end of the gastric band is held in place by the grasping end effector during the act of translating the hook member proximally, wherein the grasping end effector remains stationary as the hook member is translated in the second direction.

17. The method of claim 16, further comprising:
(a) forming a tunnel through tissue near a patient's gastroesophageal junction, wherein the act of forming a tunnel comprises using the grasping end effector to form the tunnel through blunt dissection; and
(b) pulling the gastric band through the formed tunnel, wherein the act of pulling the gastric band through the formed tunnel comprises grasping the gastric band with the grasping end effector.

18. The method of claim 16, wherein the first end of the gastric band comprises a first member defining an aperture, wherein the second end of the gastric band comprises a suture loop and second member configured to pass through the aperture, wherein the first member and the second member together define the latching mechanism;
wherein the act of grasping the first end of the gastric band with the grasping end effector comprises grasping the first member of the gastric band;
wherein the act of engaging the second end of the gastric band with the hook member comprises advancing the hook member distally and guiding the hook member through the aperture to engage the suture loop with the hook member; and
wherein the act of translating the hook member proximally relative to the shaft comprises pulling the hook member, the suture loop, and the second member of the gastric band through the aperture to engage the second member with the first member.

* * * * *